United States Patent [19]

Lee et al.

[11] Patent Number: 4,782,027
[45] Date of Patent: Nov. 1, 1988

[54] PROTEIN DETECTION BY NEGATIVE STAINING

[75] Inventors: Christopher Lee; Andrew Levin, both of Cambridge, Mass.

[73] Assignee: President and Fellows of Harvard College, Cambridge, Mass.

[21] Appl. No.: 7,136

[22] Filed: Jan. 22, 1987

[51] Int. Cl.⁴ .......................................... G01N 33/00
[52] U.S. Cl. ..................................... 436/86; 436/169; 436/174; 436/905; 530/417; 530/344; 530/395
[58] Field of Search ................ 436/86, 87, 88, 164, 436/169, 174, 175, 176, 177, 178, 515; 530/417, 344, 395

[56] References Cited

U.S. PATENT DOCUMENTS

| | | | |
|---|---|---|---|
| 3,873,433 | 3/1975 | Seidel et al. | 204/180 |
| 3,892,841 | 7/1975 | Barg, Jr. | 424/12 |
| 4,116,633 | 9/1978 | Mia | 23/230 |
| 4,405,720 | 9/1983 | Merril | 436/86 |
| 4,416,998 | 11/1983 | Adams et al. | 436/86 |
| 4,434,234 | 2/1984 | Adams et al. | 436/86 |
| 4,468,466 | 8/1984 | Morrissey | 436/86 |

OTHER PUBLICATIONS

Margerum, Pure & Appl. Chem., "Metal Peptide Complexes", 55:23 (1983).

Hager et al., Analytical Biochem., "Elution of Proteins from Sodium Dodecyl Sulfate-...", 109:76 (1980).
Switzer et al., Analytical Biochem., "A Highly Sensitive Silver Stain for Detecting Proteins and Peptides in Polyacrylamide Gels", 98:231 (1979).
Higgins, Analytical Biochem., "Rapid Visulization of Protein Bands in Preparative SDS–Polyacrylamide Gels", 93:257 (1979).
Margerum et al., Bioinorganic Chem.–II, "Copper (II)- -and Copper(III)–Peptide Complexes", 162:281 (1977).
Freeman, Advances in Protein Chem., "The Use of Model Compounds", 22:258 (1967).
Casero, Electrophoresis, "Negative Aurodye for Polyacrylamide Gels: The Impossible Stain", 6:367 (1985).

*Primary Examiner*—Barry S. Richman
*Assistant Examiner*—Lyle A. Alexander

[57] ABSTRACT

A polypeptide is located in a gel matrix by treating the matrix with a negative staining agent (i.e. an agent that stains the gel more intensely in regions devoid of polypeptides, so that gel areas exhibiting reduced staining intensity are indicative of the presence of polypeptide). Specifically, the staining agent comprises a copper or cobalt salt, and a detergent. The term polypeptide is used to include polypeptides of all sizes, including proteins and glycoproteins. The polypeptide can be purified by applying it to a gel matrix, causing it to run into the matrix, applying the above-described staining agent and then eluting the polypeptides from the matrix.

18 Claims, 1 Drawing Sheet

PROTEIN DETECTION BY NEGATIVE STAINING

This invention was made with Government support in the form of Grant No. 5R01GM31579 from the National Institute of General Medical Sciences and the National Institute of Health and the Government has certain rights in the invention.

BACKGROUND OF THE INVENTION

This invention relates to methods for detecting polypeptides in gel matrices.

Polyacrylamide gel electrophoresis is one of the major methods for separating polypeptides based on their relative size and overall charge. After separation, the location of the polypeptides in the gel is determined by staining the polypeptides; alternatively, the polypeptides may be prelabelled, for example, by radioisotopes, and their location determined by autoradiography.

One of the most common polypeptide stains is Coomassie blue. Another stain is silver, for example as described by Morrissey (U.S. Pat. No. 4,468,466). Silver staining is about one hundred-fold more sensitive than Coomassie blue staining. Hager et al. (1980, Anal. Bioc. 109:76) disclose staining gels using 0.25 M KCl and 1 mM DTT (dithiothreitol).

It is also possible to stain the polyacrylamide gel rather than the polypeptides, so that the polypeptide bands appear as transparent (or clear) regions within a white (or opaque) gel. For example, Higgens et al. (1978, Anal. Biol. 93:257) disclose staining polyacrylamide gels containing 0.1% SDS (sodium dodecyl sulfate) with 4M sodium acetate. In place of sodium acetate, Higgins discloses use of NaCl, KCl, NH$_4$Cl, (NH$_4$)$_2$SO$_4$ and potassium acetate.

Casero et al. (1985, Electrophoresis 6:367) disclose the use of colloidal gold as a negative stain.

Barg (U.S. Pat. No. 3,892,841) describes the use of soluble metal salts of zinc or copper to enhance the visibility of immunodiffusion precipitin bands. Precipitated protein is positively stained with CuCl$_2$ in the presence of Tris buffer between pH5.5 and 7.5.

SUMMARY OF THE INVENTION

The invention generally features a method for detecting a polypeptide in a gel matrix by treating the matrix with a negative staining agent (i.e. an agent that stains the gel more intensely in regions devoid of polypeptide than in regions containing polypeptides, so gel areas exhibiting reduced staining intensity are indicative of the presence of polypeptide). Specifically, the staining agent comprises a copper or cobalt salt, and a detergent. The term polypeptide is used to include polypeptides of all sizes, including proteins and glycoproteins.

In a second aspect, the invention features purifying a polypeptide by applying it to a gel matrix, causing it to run into the matrix, treating the matrix with the above-described staining agent, and removing the polypeptide from the area of the matrix exhibiting reduced staining intensity.

In a third aspect, the invention features a kit comprising at least one container for the staining agents which comprise a copper or cobalt salt, a detergent and a base.

In preferred embodiments of the three aspects, the matrix is polyacrylamide (e.g. 4–20% by weight) or agarose, and the staining agent includes a water soluble primary amine-containing base (e.g. Tris) and a large (at least six carbon atoms) anionic detergent such as sodium dodecylsulphate (SDS). The preferred copper or cobalt salts are water soluble, e.g. CuCl$_2$ or CoCl$_2$.

The invention provides a particularly easy, non-destructive, sensitive method for visualizing polypeptides and proteins in gels, and for recovering them in good yield without the agent causing irreversible immobilization of the polypeptide. Further, the staining agent reversibly immobilizes the polypeptide within the gel matrix.

Other features and advantages of the invention will be apparent from the following description of the preferred embodiments and the claims.

DESCRIPTION OF THE PREFERRED EMBODIMENTS

The drawings will be briefly described first.

Drawings

Figure 1:
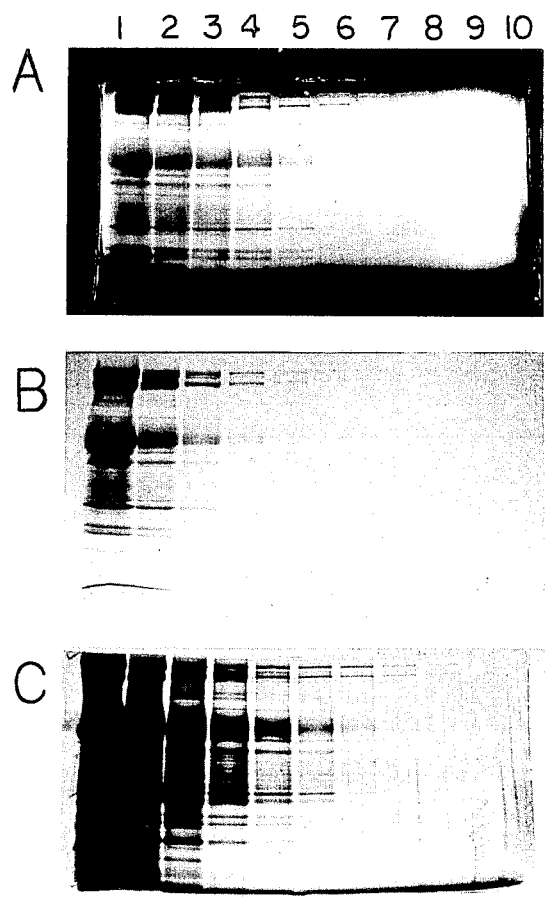
Figure 2:
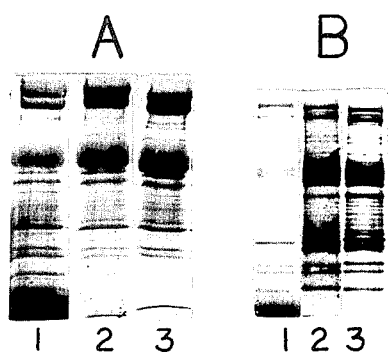

FIG. 1 is a photograph of human erythrocyte ghost proteins resolved in 5–15% gradient SDS-polyacrylamide gels and stained with: A—Coomassie brilliant blue R250; B:CuCl$_2$; or C—silver;

FIG. 2 is a photograph of human erythrocyte ghost proteins resolved in a 5–15% gradient polyacrylamide gel, stained with CuCl$_2$ (lane 1 of A and B), and then stained with Coomassie blue (A, lane 2) or silver (B, lane 2); or stained with Coomassie blue (A, lane 3) or silver (B, lane 3).

Structure

1. Gel Matrix

Polypeptides can be separated from each other according to their molecular weight, isoelectric point or overall shape, using conventional methods. Generally these methods involve separation in a gel matrix, such as polyacrylamide or agarose. While not being bound to any particular theory, it appears that the gel matrix used to separate polypeptides, prior to staining by the method of this invention, is not crucial since the matrix itself is not involved directly in the staining reaction.

2. Staining agent

Generally the staining agent useful in this invention is one that will form a visible (opaque) precipitate within the surface of the gel matrix, except at locations having polypeptides. That is, the agent causes a background opacity within the matrix. This staining agent is generally a mixture of components which together react to form a precipitate. At least one of the components of the staining agent must be able to bind to polypeptides. The ability to distinguish polypeptide from non-polypeptide containing areas in the gel is related to the staining agent's ability to bind polypeptide. It appears that when this component of the staining agent binds to polypeptides in the gel matrix, it is not available to complex with the other components and thus no precipitate is formed in these locations. At least one of the other components has an affinity for this polypeptide-binding component. One example of a staining agent is a mixture of Tris, SDS (which is a mixture of anionic detergent molecules having 12–14 carbon atoms) and a copper or cobalt salt; although other suitable primary amine-containing base may be substituted for Tris, and any other suitable large detergents (e.g., having at least six carbon atoms and being anionic, cationic or non-ionic, but preferably anionic) may be substituted for SDS, e.g., sodium cetylsulfate (having sixteen carbon atoms).

In summary, the staining agent of the invention is a negative-stain which does not involve labelling of the gel, rather it involves production of a background precipitate within the gel matrix. Formation of the precipitate is inhibited by the presence of polypeptide. The precipitate is deposited on or within the gel matrix, but the matrix itself is an inert and inactive element in the staining reaction.

Methods

1. Detecting polypeptides within gel matrices

In general the polypeptides to be detected are caused to run into the gel matrix by standard procedure, such as electrophoresis or chromatography. The gels are preferably stained immediately and the polypeptides thereby immobilized within the gel matrix. Staining involves soaking the gel matrix (which may already contain some of the components of the staining agent) in a solution of the remaining components of the staining agent, for about 5 minutes. At this point the locations of polypeptides are visible as clear areas in the gel matrix. Photographs showing their locations are readily prepared by standard procedure. Briefly, the photograph may be taken against a dark background with side lighting. The staining process reversibly immobilizes the polypeptides in the gel matrix, that is it prevents diffusion of the polypeptides within the matrix.

2. Eluting polypeptides from a gel matrix

The clear area containing a desired polypeptide is generally excised from the gel matrix and the polypeptide remobilized, to reverse the immobilization caused by the staining agent, by incubation in a solution which removes at least one of the components of the staining agent from the polypeptide region. For example a chelating agent, such as EDTA, will remove the divalent metal cations such as $Cu^{2+}$ or $Co^{2+}$, or an excess of other components of the staining agent, such as SDS or Tris will perform the same function. The polypeptide then can be removed from the matrix by standard procedures, such as electroelution or diffusion.

EXAMPLE 1

Staining polyacrylamide gels

Human erythrocyte ghosts were prepared according to Dodge et al. (100 Arch. Bioc. Biop. 119, 1963) and loaded onto a 5–15% gradient SDS-polyacrylamide gel prepared according to Laemmli (227 Nature 680, 1970, i.e. a gel containing 5–15% by weight of acrylamide). Briefly, the running gel was prepared with 0.19M, Tris/HCl, pH8.8 and 0.1% SDS, and overlaid with a 5% stacking gel prepared with 0.13M, Tris/PO$_4$. (Tris/Cl gives equivalent results), pH6.8 and 0.1% SDS. The gel was 5 cm $\times$ 8 cm $\times$ 0.75 mm and the polypeptides were electrophoresed in a minigel apparatus (Hoefer Scientific Co., San Fransisco, CA). Immediately after electrophoresis the protein bands were visualized by rinsing the gel for several seconds in distilled water and then transferring the gel to a plastic tray containing 0.3 M CuCl$_2$. After gentle agitation for 5 min. at room temperature (20°–25° C.) the gel was removed, rinsed in distilled water, and stored in distilled water.

For comparative purposes the same protein samples were electrophoresed in parallel gels and stained by standard procedures with either 0.05% Coomassie brilliant blue R250 in 25% isopropanol/11% alcohol and destaining in 10% isopropanol/10% alcohol; silver stain according to the method of Oakley et al. (105 Anal. Bioc. 361, 1980); or with KCl or sodium acetate according to the method of Hager et al., supra and Higgens et al., supra, respectively.

To photograph the negatively stained copper gel, the gel was placed on a glass sheet coated with black paint, illuminated from above and photographed using Kodak 2415 film. The results are shown in FIG. 1. Lanes 1–10 contain respectively 30, 10, 3.3, 1.1, 0.37, 0 12, 0.040, 0.014, 0.005 and 0.0015 $\mu$g of protein. After treatment of the SDS and tris containing gel with CuCl$_2$, a white-blue precipitate was present throughout the gel, except in areas containing protein, which remained clear and colorless. This staining procedure is generally more sensitive than Coomassie blue, KCl, or sodium acetate and less sensitive than silver staining. The various staining methods visualized substantially the same polypeptides.

The conditions which are important for gel staining, as described above, include the buffer pH, since an acid pH (below about 7.0) does not allow the blue-white precipitate to develop. Nevertheless, acid gels can be stained using CuCl$_2$ if they are first incubated in a Tris/SDS buffer (19mM Tris pH8.8, 0.1% SDS) so that the buffer locally surrounding the gel matrix is suitable for staining—i.e. it contains the Tris, at high pH, and SDS components of the staining agent. Although CuCl$_2$ is preferred, other salts such as CuSO$_4$ and CoCl$_2$ are suitable substitutes. Linear polyacrylamide gels from any polyacrylamide concentration (e.g., 4–20%) and any thickness can be stained by this method. Once stained, these gels may be stored in water at room temperature (20°–25° C.) with no visible change in the staining pattern for several months. The proportions of Tris, SDS and CuCl$_2$ in the staining agent mixture can be varied, for example, Tris from 10–200mM, SDS from 0.05–0.5% and CuCl$_2$ from 0.1–1M.

EXAMPLE 2

Staining CuCl$_2$ stained gels

CuCl$_2$-stained gels of human erythrocyte ghost proteins can be stained with Coomassie Blue or Silver, as if no CuCl$_2$ treatment had been used, without a separate destaining step. The results are shown in FIG. 2. The resulting stained gels are indistinguishable from gels which have not previously been stained with the CuCl$_2$-containing staining agent.

EXAMPLE 3

Elution of polypeptides from CuCl$_2$ stained gels

One of the important features of the staining method of this invention is that it allows ready removal of a desired polypeptide from a gel matrix. The removal is achieved by standard procedures after a brief treatment of the gel to mobilize the polypeptides within it.

The polypeptides in gels or excised gel slices stained with the copper staining agent were mobilied by incubation with gentle agitation in two changes of 0.25 M EDTA/0.25 M Tris-HCl, pH 9.0, for 30 minutes. Gels or gel slices thus treated were then incubated in 20 mM Tris base/150 mM glycine/0.01% SDS for 10 min., and the polypeptides electroeluted in the same buffer. Electroelution was performed in an ISCO electrophoretic concentrator (ISCO, P.0. Box 5347, Lincoln, Neb.) for 30–60 min at 100V.

Copper-stained gels can be stored for months in distilled water at room temperature without significant polypeptide diffusion or loss, and the polypeptide bands can be readily eluted, after polypeptide mobilization in a basic Tris-HCl/EDTA solution.

As a test, we recovered 90% (standard deviation, S.D.=1.3%, sample number, n=3) of a sample of $^{125}$I-brain clathrin heavy chain (MW 180,000; purified according to Keen et al., 16 Cell 303, 1979, and iodinated with Bolton-Hunter reagent, 133 Bioc. J. 529, 1973) electroeluted from a copper stained gel. Comparable recoveries of clathrin (97%, S.D.=0.8%, n=3) were obtained from an identical unstained gel slice. Only small amounts of protein were lost during the 30 minute polypeptide mobilizing step (2.3%, S.D.=4, n=3) or were found to remain in the gel slice after elution (6.1%, S.D.=1.5%, n=3). We have eluted a variety of other polypeptides from copper stained gels with similarly high recovery, including erythrocyte spectrin and band 4.1 (the first sub-band of erythrocyte polypeptides running fourth from the top of the major erythrocyte polypeptide bands), ovalbumin, and actin. The recovered polypeptides migrate as single bands upon re-electrophoresis, without discernible breakdown products. Polypeptide was also eluted, after mobilization, from macerated gel slices by simple diffusion (Hager et al., 109 Anal. Bioc. 76, 1980) with similar results. Eluted polypeptides were injected into mice with no apparent toxic effects. After mobilization, the polypeptides can also be electrotransferred from copper stained gels to nitrocellulose membranes (for western blotting).

EXAMPLE 4

Formation of precipitate with staining agent

In order to determine the chemical reactions that may be involved with the staining procedure of the invention, test tube reactions were carried out. Tris-SDS solutions (190mM Tris pH8.8, 0.1%SDS) were prepared with or without 2mg/ml ovalbumin. Ovalbumin and $CuCl_2$ alone form a strongly yellow colored insoluble complex. Tris-SDS and $CuCl_2$ form a whitish blue sparingly soluble complex. The whitish-blue complex precipitates out only as the molar ratio approaches $1:1.5:1.2\times10^{-4}$ ($Cu^{2+}$:Tris:SDS). When ovalbumin (2mg/ml) is present, the $CuCl_2$ preferentially complexes with the protein to form the yellow complex, however this yellow complex dissolves upon vortexing. These results indicate that the $CuCl_2$ preferentially complexes with proteins rather than Tris-SDS. Thus the staining procedure of the invention apparently occurs because in regions containing polypeptide, the polypeptide complexes with the $CuCl_2$ (or equivalent salt), preventing the formation of the white-complex. In areas where no polypeptide is present, the white (opaque) complex forms and precipitates out on the gel matrix.

pH is apparently important to the staining reaction. This is because Tris has a pK of 8.06, and is only unprotonated at higher pHs, having amino groups which can then complex with divalent cations, such as $Cu^{2+}$. At lower pHs these amino groups are not available. Use of other buffers having lower pKs may allow the staining reactions to occur at a lower pH.

Other embodiments are within the following claims.

We claim:

1. A method for detecting a polypeptide in a gel matrix, comprising treating said matrix with a staining agent that stains said gel more intensely in regions devoid of polypeptide than in regions containing polypeptide, regions of said gel exhibiting reduced intensity being indicative of the presence of polypeptide, wherein said staining agent comprises a water soluble copper or cobalt salt and a detergent and subsequently detecting a region of said matrix comprising said polypeptide as a region exhibiting reduced staining intensity.

2. A method of purifying a polypeptide, comprising:
   (a) applying said polypeptide to a gel matrix;
   (b) causing said polypeptide to run into said matrix;
   (c) treating said matrix with a staining agent that stains said gel more intensely in regions devoid of polypeptide than in regions containing polypeptide, regions of said gel exhibiting reduced intensity being indicative of the presence of polypeptide, wherein said staining agent comprises a water soluble copper or cobalt salt and a detergent;
   (d) and detecting a region of said matrix comprising said polypeptide as a region exhibiting reduced staining intensity; and thereafter
   (e) eluting said polypeptide from said area of said gel exhibiting reduced staining intensity.

3. The method of claim 1 or 2 wherein said gel matrix is a polyacrylamide gel.

4. The method of claim 3 wherein said polyacrylamide gel has between 4–20% by weight polyacrylamide.

5. The method of claim 1 or 2 wherein said staining agent produces a background precipitate within said matrix.

6. The method of claim 1 or 2 wherein said gel matrix is an agarose gel.

7. The method of claim 1 or 2 wherein said gel matrix comprises SDS and Tris buffer.

8. The method of claim 1 or 2 wherein said copper or cobalt in said salt has a valence of +2.

9. The method of claim 8 wherein said salt is $CuCl_2$.

10. A kit, comprising:
    a series of three containers that contain the precursors of a staining agent that stains a gel matrix more intensely in regions devoid of polypeptide than in regions containing polypeptide, regions of the gel exhibiting reduced intensity being indicative of the presence of polypeptide, wherein said precursors comprises a first container containing a material consisting essentially of a copper or cobalt salt, a second container containing a detergent and a third container containing a base.

11. The kit of claim 10 wherein said detergent is SDS.

12. The kit of claim 11 wherein said copper or cobalt in said salt has a valence of +2.

13. The kit of claim 11 wherein said salt is $CuCl_2$.

14. The kit of claim 11 wherein said base comprises a primary amine-containing base.

15. The kit of claim 14 wherein said base is Tris(hydroxymethyl)aminomethane.

16. The kit of claim 10 further comprising means therein for providing a gel matrix.

17. The kit of claim 16 wherein said matrix is a material selected from the group consisting of polyacrylamide and agarose.

18. The kit of claim 17 wherein said polyacrylamide gel has between 4–20% polyacrylamide by weight.

* * * * *